US012286594B2

(12) United States Patent
Ye et al.

(10) Patent No.: US 12,286,594 B2
(45) Date of Patent: *Apr. 29, 2025

(54) FLUIDIZED BED REACTOR, DEVICE AND METHOD FOR PREPARING LOW-CARBON OLEFINS FROM OXYGEN-CONTAINING COMPOUND

(71) Applicant: DALIAN INSTITUTE OF CHEMICAL PHYSICS, CHINESE ACADEMY OF SCIENCES, Dalian (CN)

(72) Inventors: Mao Ye, Dalian (CN); Tao Zhang, Dalian (CN); Jinling Zhang, Dalian (CN); Shuliang Xu, Dalian (CN); Hailong Tang, Dalian (CN); Xiangao Wang, Dalian (CN); Cheng Zhang, Dalian (CN); Jinming Jia, Dalian (CN); Jing Wang, Dalian (CN); Hua Li, Dalian (CN); Chenggong Li, Dalian (CN); Zhongmin Liu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 51 days.

This patent is subject to a terminal disclaimer.

(21) Appl. No.: 17/784,647

(22) PCT Filed: Oct. 16, 2020

(86) PCT No.: PCT/CN2020/121553
§ 371 (c)(1),
(2) Date: Jun. 12, 2022

(87) PCT Pub. No.: WO2022/077452
PCT Pub. Date: Apr. 21, 2022

(65) Prior Publication Data
US 2023/0002682 A1    Jan. 5, 2023

(51) Int. Cl.
*C10G 3/00* (2006.01)
*B01D 45/16* (2006.01)
(Continued)

(52) U.S. Cl.
CPC ............... *C10G 3/57* (2013.01); *B01D 45/16* (2013.01); *B01J 8/1827* (2013.01); *B01J 8/1836* (2013.01);
(Continued)

(58) Field of Classification Search
CPC .............. C10G 3/57; C10G 2300/4093; C10G 2400/20; B01D 45/16; B01J 8/1827;
(Continued)

(56) References Cited

U.S. PATENT DOCUMENTS 5,714,662 A      2/1998  Vora et al.
2007/0203383 A1*  8/2007  Bozzano ................... C07C 1/20
                                                      585/639

FOREIGN PATENT DOCUMENTS

CN        1382198 A      11/2002
CN      101259433 A       9/2008
(Continued)

OTHER PUBLICATIONS

Translation of CN101941876A (Year: 2009).*

*Primary Examiner* — Ali Z Fadhel
(74) *Attorney, Agent, or Firm* — Bayramoglu Law Offices LLC

(57) ABSTRACT

A fluidized bed reactor, a device, and a method for producing low-carbon olefins from oxygen-containing compound are provided. The fluidized bed reactor includes a reactor shell, a reaction zone, a coke control zone and a delivery pipe, where there are n baffles arranged in the coke control zone, and the n baffles divide the coke control zone into n sub-coke control zones which include a first sub-coke control zone, a
(Continued)

second sub-coke control zone, and an nth sub-coke control zone; at least one catalyst circulation hole is provided on each of the n-1 baffles, so that the catalyst flows in an annular shape in the coke control zone, where n is an integer. The device and method can be adapted to a new generation of DMTO catalyst, and the unit consumption of production ranges from 2.50 to 2.58 tons of methanol/ton of low-carbon olefins.

20 Claims, 2 Drawing Sheets

(51) Int. Cl.
*B01J 8/18* (2006.01)
*B01J 29/85* (2006.01)
*B01J 31/06* (2006.01)
*C07C 1/24* (2006.01)

(52) U.S. Cl.
CPC ............. *B01J 8/1845* (2013.01); *B01J 29/85* (2013.01); *B01J 31/06* (2013.01); *C07C 1/24* (2013.01); *B01J 2208/00017* (2013.01); *B01J 2208/0084* (2013.01); *C07C 2529/85* (2013.01); *C07C 2531/06* (2013.01); *C10G 2300/4093* (2013.01); *C10G 2400/20* (2013.01)

(58) Field of Classification Search
CPC ........ B01J 8/1836; B01J 8/1845; B01J 29/85; B01J 31/06; B01J 2208/00017; B01J 2208/0084; B01J 8/28; B01J 2208/00938; B01J 8/1863; B01J 8/26; B01J 2229/12; B01J 38/30; B01J 38/32; B01J 8/24; B01J 29/90; C07C 1/24; C07C 2529/85; C07C 2531/06; C07C 1/20; C07C 11/02; Y02P 20/52; Y02P 20/584; Y02P 30/20; Y02P 30/40

See application file for complete search history.

(56) References Cited

FOREIGN PATENT DOCUMENTS

| | | | |
|---|---|---|---|
| CN | 101696145 A | 4/2010 |
| CN | 101941876 A | 1/2011 |
| CN | 102276395 A | 12/2011 |
| CN | 103073377 A | 5/2013 |
| CN | 103772092 A | 5/2014 |
| CN | 104672040 A | 6/2015 |
| CN | 104672044 A | 6/2015 |
| CN | 107961743 A | 4/2018 |
| CN | 111099945 A | 5/2020 |
| EP | 3721995 A1 | 10/2020 |
| KR | 20020052184 A | 7/2002 |
| KR | 20160093676 A | 8/2016 |
| RU | 2412146 C1 | 2/2011 |
| RU | 2632905 C1 | 10/2017 |
| WO | 2015081489 A1 | 6/2015 |

* cited by examiner

FLUIDIZED BED REACTOR, DEVICE AND METHOD FOR PREPARING LOW-CARBON OLEFINS FROM OXYGEN-CONTAINING COMPOUND

CROSS REFERENCE TO THE RELATED APPLICATIONS

This application is the national phase entry of International Application No. PCT/CN2020/121553, filed on Oct. 16, 2020, the entire contents of which are incorporated herein by reference.

TECHNICAL FIELD

The present application relates to a fluidized bed reactor, a device, and a method for preparing low-carbon olefins from oxygen-containing compound, and belongs to the field of chemical catalysis.

BACKGROUND

Methanol-to-olefin technology (MTO) mainly includes DMTO (methanol-to-olefin) technology of Dalian Institute of Chemical Physics, Chinese Academy of Sciences and MTO technology of UOP Company of the United States. In 2010, the Shenhua Baotou methanol-to-olefin plant using DMTO technology was completed and put into operation. This is the world's first industrial application of MTO technology. As of the end of 2019, 14 DMTO industrial plants have been put into production, with a total production capacity of about 8 million tons of low-carbon olefins per year.

In recent years, DMTO technology has been further developed, and a new generation of DMTO catalyst with better performance have gradually begun industrial applications, creating higher benefits for DMTO plants. The new generation of DMTO catalyst has higher methanol processing capacity and low-carbon olefin selectivity. It is difficult for the existing DMTO industrial devices to take full advantage of the advantages of the new generation of DMTO catalyst. Therefore, it is necessary to develop a DMTO device and production method that can meet the needs of a new generation of DMTO catalyst with high methanol processing capacity and high selectivity of low-carbon olefins.

SUMMARY

According to one aspect of the present application, there is provided a fluidized bed reactor. The fluidized bed reactor can achieve online modification of the DMTO catalyst through coke control reaction. The modification in the present application refers to the control of coke content in the DMTO catalyst, coke content distribution and coke species, so as to control the performance of DMTO catalyst and improve the selectivity of low-carbon olefins.

The low-carbon olefins described in the present application refer to ethylene and propylene.

The applicant's research found that the main factors affecting the activity of the DMTO catalyst and the selectivity of low-carbon olefins are the coke content, coke content distribution and coke species in the catalyst. When the average coke content in the catalyst is the same, if the coke content distribution is narrow, the selectivity of low-carbon olefins and the activity of the catalyst are high. The coke species in the catalyst include polymethyl aromatic hydrocarbons and polymethyl cycloalkanes, among which polymethylbenzene and polymethylnaphthalene can promote the production of ethylene. Therefore, control of the coke content, the coke content distribution and the coke species in the catalyst is the key to controlling the activity of the DMTO catalyst and improving the selectivity of low-carbon olefins.

According to the first aspect of the present application, there is provided a fluidized bed reactor. The fluidized bed reactor includes a reactor shell, a reaction zone, a coke control zone and a delivery pipe;

the reactor shell includes a lower shell and an upper shell, the lower shell enclose a reaction zone, the delivery pipe is disposed above the reaction zone and in communication with the reaction zone, the outer periphery of the delivery pipe is provided with the upper shell, the upper shell and the delivery pipe enclose to form a cavity including a coke control zone;

the upper part of the delivery pipe is provided with a gas outlet; the reaction zone includes a reaction raw material inlet and a coke controlled catalyst inlet;

the coke control zone includes a catalyst inlet, a coke controlled catalyst outlet, a coke control gas outlet, and a coke control raw material inlet;

the coke control zone is an annular cavity; there are n baffles arranged in the coke control zone, and the n baffles divide the coke control zone into n sub-coke control zones which include a first sub-coke control zone, a second sub-coke control zone, and an nth sub-coke control zone;

at least one catalyst circulation hole is provided on each of n−1 baffles, so that the catalyst flows in an annular shape in the coke control zone, wherein n is an integer;

the catalyst inlet is arranged in the first sub-coke control zone, the coke controlled catalyst outlet is arranged in the nth sub-coke control zone, and the coke control gas outlet is arranged between two adjacent baffles.

When the coke control zone contains only one zone, the residence time distribution of the catalyst entering the coke control zone is similar to the residence time distribution in a perfectly mixed flow reactor. Under this condition, the coke content uniformity on the obtained coke controlled catalyst granules is poor. In other words, some catalyst granules have lower coke content while some other catalyst granules have higher coke content, resulting in lower average activity and lower average selectivity of the catalyst. In the present application, by configuring the coke control zone and installing baffles along the radial direction in the coke control zone to divide the coke control zone into several sub-coke control zones, thereby controlling the residence time distribution of the catalyst entering the coke control zone, making the coke content distribution in the coke controlled catalyst narrow, and possessing higher average activity and higher average selectivity. At the same time, the use of sub-zone control is also beneficial to control the coke species and coke content on the coke controlled catalyst.

Optionally, the first baffle is not provided with any catalyst circulation hole, while each one of the second baffle to the nth baffle is provided with catalyst circulation hole(s).

Optionally, the diameter of the coke control zone in the present application is smaller than the diameter of the reaction zone.

Preferably, the diameter of the coke control zone increases from bottom to top.

Optionally, the first sub-coke control zone divided by the first baffle and the second baffle is provided with a catalyst inlet for the coke control zone;

the nth sub-coke control zone divided by the first baffle and the nth baffle is provided with a coke controlled catalyst delivery pipe, which is in communication with the reaction zone, one end of which is arranged at the outlet of the coke controlled catalyst, and the other end of which is arranged in the reaction zone.

Preferably, a coke controlled catalyst slide valve is further provided on the coke controlled catalyst delivery pipe to control the circulation of the catalyst.

A coke control zone distributor is arranged below the sub-coke control zone, and the coke control gas outlet is connected to the delivery pipe by a coke control zone gas delivery pipe.

In the present application, by configuring the coke control zone, installing baffles arranged concentrically in sequence in the coke control zone and configuring circulation holes on the baffles, the coke control zone is divided into several sub-coke control zones so that the catalyst can flow in an annular shape in the coke control zone, thereby controlling the residence time of the catalyst entering the coke control zone and the way of coke control. That is to say, when coke control is performed in each sub-zone, the content of the catalyst in the control space is relatively uniform, so that the coke content distribution in the catalyst is narrow, and the coke species and coke content on the catalyst are also controlled. It is avoided that some catalyst granules have lower coke content, and some other catalyst granules have higher coke content, resulting in a wide distribution of catalyst coke content.

Optionally, $2 \leq n \leq 10$.

Specifically, the number of catalyst circulation holes provided on the baffle may be one or more, which is not strictly limited in the present application. When a plurality of catalyst circulation holes are provided, the relative positions of the catalyst circulation holes are not strictly limited in the present application. For example, a plurality of catalyst circulation holes may be arranged in parallel, or may be arranged randomly.

In the present application, the shape of the coke controlled catalyst delivery pipe is not strictly limited, as long as it can be ensured that the coke controlled catalyst delivery pipe can transport the coke controlled catalyst to the reaction zone. For example, the coke controlled catalyst delivery pipe can be a long pipe with a bent structure. Of course, the coke controlled catalyst delivery pipe can be in other suitable shapes.

Preferably, a coke control zone distributor is provided below each sub-coke control zone. In this way, it is possible to realize that the entire coke control material enters the coke control zone uniformly, avoid the uniformity of the coke control material between the sub-zones, thereby better realizing the narrow distribution of the coke content in the catalyst.

Optionally, the cross section of the coke control zone is annular in shape, and the cross section of the sub-coke control zone is fan in shape.

Optionally, the coke control gas outlet is connected to the delivery pipe by a coke control zone gas delivery pipe.

Optionally, a coke control zone distributor is provided at the bottom of the sub-coke control zone;

the coke control raw material inlet is in communication with the coke control zone distributor, or the coke control raw material inlet is located below the coke control zone distributor.

Preferably, a coke control zone distributor is provided at the bottom of each sub-coke control zone.

Optionally, a reaction zone distributor is arranged at the reaction raw material inlet, and the reaction zone distributor is arranged at the bottom of the reaction zone.

Specifically, the reaction zone distributor is used to feed reaction raw materials in the reaction zone.

Specifically, in the present application, the reaction raw material refers to the one including oxygen-containing compound.

Optionally, the fluidized bed reactor further includes a spent catalyst zone which is arranged above the coke control zone and sleeved on the outer periphery of the delivery pipe, and a partition plate is provided between the spent catalyst zone and the coke control zone; a spent catalyst zone distributor is arranged at the bottom of the spent catalyst zone.

Optionally, the spent catalyst zone further contains a heat extractor for fluidized bed reactor.

Optionally, the fluidized bed reactor further includes a gas-solid separation zone which is arranged above the spent catalyst zone and sleeved on the outer periphery of the delivery pipe;

the gas-solid separation zone is provided with a gas-solid separation device; The spent catalyst zone is in communication with the gas-solid separation zone.

Optionally, the gas-solid separation device includes a first gas-solid separation device and a second gas-solid separation device;

an inlet of the first gas-solid separation device is in communication with the delivery pipe, and a catalyst outlet of the first gas-solid separation device is located in the spent catalyst zone;

a catalyst outlet of the second gas-solid separation device is also provided in the spent catalyst zone.

Optionally, the fluidized bed reactor further includes a product gas delivery pipe and a gas collection chamber which are arranged on the upper part of the reactor shell, the product gas delivery pipe is arranged at the top of the reactor shell, and the product gas delivery pipe is connected to the top of the gas collection chamber;

the gas outlet of the second gas-solid separation device is connected to the gas collection chamber, and the gas outlet of the first gas-solid separation device is connected to the gas collection chamber.

Optionally, the fluidized bed reactor further includes a spent catalyst circulation pipe which is arranged outside the reactor shell.

The inlet of the spent catalyst circulation pipe is connected to the spent catalyst zone, and the outlet of the spent catalyst circulation pipe is connected to the bottom of the reaction zone.

Optionally, the spent catalyst circulation pipe is also provided with a spent catalyst circulation slide valve for controlling the circulation of the spent catalyst.

According to a second aspect of the present application, there is also provided a method for preparing low-carbon olefins from oxygen-containing compound, which is carried out by using at least one of the above-mentioned fluidized bed reactors.

Optionally, the method includes following steps: feeding the coke control raw material and the catalyst from the regenerator into the coke control zone to react to generate coke controlled catalyst and coke control product gas;

the catalyst forms annular flow through the catalyst circulation hole(s) on the baffle.

Optionally, the method includes following steps:
(1) feeding the coke control raw material from the coke control zone distributor into the coke control zone, and feeding the catalyst from the catalyst inlet to the coke control zone, wherein the coke control raw material and the catalyst contact to react in the coke control zone to generate the coke controlled catalyst and the coke control product gas; wherein the coke controlled catalyst enters the reaction zone via the coke controlled catalyst outlet, and the coke control product gas enters the delivery pipe via the coke control gas outlet;

(2) feeding the raw material including an oxygen-containing compound into the reaction zone via the reaction raw material inlet, to contact the with coke control catalyst, to obtain a stream A including low-carbon olefins.

Optionally, the coke control raw material includes $C_1$-$C_6$ hydrocarbon compound.

Preferably, said hydrocarbon compound is at least one of $C_1$-$C_6$ alkanes and $C_1$-$C_6$ olefins.

Optionally, the coke control raw material further includes at least one of hydrogen, alcohol compound, and water;

the total weight content of the alcohol compound and water in the coke control raw material is greater than or equal to 10 wt % and less than or equal to 50 wt %.

Preferably, the alcohol compound is at least one of methanol and ethanol.

Optionally, the coke control raw materials includes: 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water;

the weight content of the hydrocarbon compound is not zero.

Optionally, the oxygen-containing compound is at least one of methanol and dimethyl ether.

Optionally, the catalyst includes SAPO molecular sieve; the coke content in the coke controlled catalyst ranges from 4 wt % to 9 wt %;

The quartile deviation of the coke content distribution in the coke controlled catalyst is less than 1 wt %.

Specifically, in the present application, the configuration of the coke control zone and the selection of the coke control process achieve that the coke content in the coke controlled catalyst ranges from 4 wt % to 9 wt %. Since the catalyst is granular in shape, the coke content in the catalyst refers to the average value of the coke content in each catalyst granule, but the coke content in each catalyst granule is actually different. In the present application, the quartile deviation of the coke content distribution in the coke controlled catalyst can be controlled to be less than 1 wt %, so that the overall coke content distribution in the catalyst is narrow, thereby improving the activity of the catalyst and the selectivity of low-carbon olefins.

Optionally, the coke species in the coke controlled catalyst include polymethylbenzene and polymethylnaphthalene;

the total weight content of the polymethylbenzene and polymethylnaphthalene in the total coke weight is ≥70 wt %;

the weight content of the coke species with a molecular weight greater than 184 in the total coke weight is ≤25 wt %;

wherein, the total coke weight refers to the total weight of coke species.

In the present application, the type of coke species and the content of coke species are also very important, and they are also one purpose of coke control. In the present application, the setting of the coke control and the selection of coke control process parameters achieve that the total content of polymethylbenzene and polymethylnaphthalene in the total coke weight is ≥70 wt %, the activity of the catalyst and the selectivity of low-carbon olefins are improved.

Optionally, the process operating conditions in the coke control zone are as follows: the apparent linear velocity of gas ranges from 0.1 m/s to 0.5 m/s, the reaction temperature ranges from 300° C. to 700° C., the reaction pressure ranges from 100 kPa to 500 kPa, and the bed density ranges from 400 kg/m$^3$ to 800 kg/m$^3$;

the process operating conditions in the reaction zone are as follows: the apparent linear velocity of gas ranges from 0.5 m/s to 7.0 m/s, the reaction temperature ranges from 350° C. to 550° C., the reaction pressure ranges from 100 kPa to 500 kPa, and the bed density ranges from 100 kg/m$^3$ to 500 kg/m$^3$.

Optionally, after step (2), the method further includes following step:

(3) mixing the stream A including low-carbon olefins and the coke control product gas flowing out of the coke control gas outlet to form a mixed stream B in the delivery pipe by which the stream B enters the first gas-solid separation device, and is then divided into a gas phase stream C and a solid phase stream D after the gas-solid separation, wherein the gas phase stream C is a gas including low-carbon olefins, and the solid phase stream D is a spent catalyst.

Optionally, the coke content in the spent catalyst ranges from 9 wt % to 13 wt %.

Optionally, after step (3), the method further includes following step:

(4) feeding the gas phase stream C into the gas collection chamber, and the solid phase stream D into the spent catalyst zone, feeding a fluidizing gas for the spent catalyst zone into the spent catalyst zone from the fluidizing gas inlet for the spent catalyst zone to contact with the spent catalyst such that the fluidizing gas for the spent catalyst zone and the spent catalyst carried by such gas form a stream E.

Optionally, the fluidizing gas for the spent catalyst zone includes at least one of nitrogen and water vapor.

Optionally, after step (4), the method further includes following step:

(5) feeding the stream E into a second gas-solid separation device to divide it into a gas phase stream F and a solid phase stream G after gas-solid separation, wherein the gas phase stream F is the fluidizing gas for the spent catalyst zone, and the solid phase stream G is the spent catalyst; feeding the gas phase stream F into the gas collection chamber and the solid phase stream G into the spent catalyst zone, and mixing the gas phase stream C and the gas phase stream F in the gas collection chamber to form product gas which then enters a section downstream via a product gas delivery pipe.

Optionally, after step (5), the method further includes following step: (6) returning the spent catalyst in the spent catalyst zone to the bottom of the reaction zone of the fluidized bed reactor through the spent catalyst circulation pipe.

Optionally, the process operating conditions in the spent catalyst zone are as follows: the apparent linear velocity of gas ranges from 0.1 m/s to 1.0 m/s, the reaction temperature ranges from 350° C. to 550° C., the reaction pressure ranges from 100 kPa to 500 kPa, and the bed density ranges from 200 kg/m$^3$ to 800 kg/m$^3$.

According to a third aspect of the present application, there is also provided a device including a fluidized bed reactor and a fluidized bed regenerator, wherein the fluidized bed reactor is in communication with the fluidized bed regenerator;

the fluidized bed reactor is at least one of the above-mentioned fluidized bed reactors.

Optionally, the fluidized bed regenerator includes a regenerator shell; the regenerator shell is provided with a spent catalyst inlet; the spent catalyst inlet is in communication with the spent catalyst zone of the fluidized bed reactor.

Preferably, the spent catalyst inlet is in communication with the spent catalyst zone of the fluidized bed reactor through a first stripper.

Further preferably, the spent catalyst zone of the fluidized bed reactor is in communication with the first stripper through a spent catalyst inclination pipe.

Optionally, the first stripper is in communication with the spent catalyst inlet through a spent catalyst delivery pipe.

Preferably, the spent catalyst delivery pipe is provided with a spent catalyst slide valve for controlling the circulation of the catalyst.

Specifically, the device for preparing low-carbon olefins from oxygen-containing compound provided in the present application includes a fluidized bed regenerator, which is used to regenerate the spent catalyst and pass the regenerated catalyst into the coke control zone to control coke, which is then passed into the reaction zone for catalytic reaction. Coke control in the catalyst can be performed online to improve production efficiency.

Optionally, the bottom of the regenerator shell is in communication with the coke control zone.

Preferably, the bottom of the regenerator shell is in communication with the coke control zone through a second stripper.

Preferably, a regenerator heat extractor is provided in the second stripper.

Optionally, a regenerator distributor is also provided in the regenerator shell; and one end of the second stripper extends into the regenerator shell.

Optionally, the second stripper is in communication with the regenerated catalyst inlet through a regenerated catalyst delivery pipe.

Preferably, a regenerated catalyst slide valve is provided on the regenerated catalyst delivery pipe.

Optionally, the fluidized bed regenerator further includes a regenerator gas-solid separation device, a regenerator gas collection chamber, and a flue gas delivery pipe;

the regenerator gas-solid separation device is provided in the regenerator shell, the regenerator gas collection chamber and the flue gas delivery pipe are provided on the upper part of the regenerator shell, the flue gas delivery pipe is provided on the top of the regenerator shell, and the flue gas delivery pipe is connected to the top of the regenerator gas collection chamber; and the gas outlet of the regenerator gas-solid separation device is connected to the regenerator gas collection chamber, and the regenerated catalyst outlet of the regenerator gas-solid separation device is provided at the lower part of the regenerator shell.

According to a fourth aspect of the present application, there is also provided a method for preparing low-carbon olefins from oxygen-containing compound, which is performed by using at least one of the above-mentioned devices.

Optionally, the method includes feeding the spent catalyst in the spent catalyst zone into the fluidized bed regenerator, and then feeding the catalyst regenerated in the fluidized bed regenerator into the coke control zone.

Optionally, the method includes following steps: (a) passing the spent catalyst through the first stripper, which is then fed into the middle of the fluidized bed regenerator after stripping;

(b) feeding a regeneration gas from a regeneration gas inlet into the bottom of the fluidized bed regenerator to contact with the spent catalyst to perform a chemical reaction to generate a stream H including flue gas and regenerated catalyst, which enters the regenerator gas-solid separation device and is divided into flue gas and regenerated catalyst after gas-solid separation, feeding the flue gas into a regenerator gas collection chamber and then into the flue gas treatment system downstream through a flue gas delivery pipe, returning the regenerated catalyst to the bottom of the fluidized bed regenerator, then into a second stripper, and into the coke control zone of the fluidized bed reactor after stripping and heat extraction.

Preferably, the coke content in the regenerated catalyst is ≤3 wt %. Optionally, the regeneration gas is at least one of oxygen, nitrogen, water vapor and air. Preferably, the regeneration gas includes 0 wt % to 100 wt % of air, 0 wt % to 50 wt % of oxygen, 0 wt % to 50 wt % of nitrogen, and 0 wt % to 50 wt % of water vapor.

Optionally, the process operating conditions in the fluidized bed regenerator are as follows: the apparent linear velocity of gas ranges from 0.5 m/s to 2.0 m/s, the regeneration temperature ranges from 600° C. to 750° C., the regeneration pressure ranges from 100 kPa to 500 kPa, and the bed density ranges from 150 kg/m$^3$ to 700 kg/m$^3$.

Optionally, the coke content in the regenerated catalyst is ≤3 wt %.

The method for preparing low-carbon olefins further includes following steps: feeding the spent catalyst in the spent catalyst zone into the fluidized bed regenerator for regeneration to produce a regenerated catalyst, and then feeding the regenerated catalyst into the coke control zone of the fluidized bed reactor to contact with the coke control raw materials to react.

Specifically, the fluidized bed reactor in the present application is divided into a reaction zone, a coke control zone, a spent catalyst zone, and a gas-solid separation zone from bottom to top. The method includes followings: a) subjecting the coke control raw material to contact with the catalyst in the coke control zone of the fluidized bed reactor to generate the coke control product gas and the coke controlled catalyst, and then feeding the coke controlled catalyst into the reaction zone of the fluidized bed reactor, and subjecting the raw material including oxygen-containing compound to contact with the coke controlled catalyst in the reaction zone to generate product gas including low-carbon olefins and the spent catalyst; b) subjecting the regeneration gas to contact with the spent catalyst in the fluidized bed regenerator to generate flue gas and regenerated catalyst, and then feeding the regenerated catalyst into the coke control zone.

The C1-C$_6$ hydrocarbon compound in the present application refers to a hydrocarbon compound with the number of carbon atoms ranging from 1 to 6.

The beneficial effects that the present application can achieve include:

(1) The catalyst in the present application can flow sequentially from the sub-zone upstream to the sub-zone downstream through the catalyst circulation hole(s) on the baffle in the coke control zone, so that ① the catalyst inventory in the coke control zone can be automatically adjusted, that is, the coke content in the catalyst can be controlled by controlling the average residence time of the catalyst in the coke control zone; and ② the residence time distribution of the catalyst can be controlled by using the configuration of n sub-coke control zones, and the residence time distribution is similar to n perfectly mixed flow reactors in series, thereby obtaining narrow distribution of the catalyst coke content.

(2) By controlling the conversion and production of coke species in the catalyst in the present application, on one hand, the remaining inactive macromolecular coke species in the catalyst are converted into small molecular coke species; on the other hand, the coke control raw materials can also enter the catalyst to generate small molecular coke species with high-activity, and the small molecular coke species are mainly polymethylbenzene and polymethylnaphthalene, which can improve the selectivity of ethylene.

(3) The method for modifying the DMTO catalyst online through the coke control reaction in the present application can obtain a coke controlled catalyst with high coke content, narrow coke content distribution, and the main components of coke species being polymethylbenzene and polymethylnaphthalene, thereby converting catalyst with low selectivity of low-carbon olefins into a coke controlled catalyst with high selectivity of low-carbon olefins.

(4) The catalyst in the present application can also be directly used to prepare low-carbon olefins from oxygen-containing compound without coke control treatment. Under the situation that the coke control treatment is not performed, the selectivity of low-carbon olefins in the product gas obtained ranges from 80 wt % to 83 wt %. Under the situation that the coke control treatment is performed and the coke controlled catalyst in the present application is used to prepare low-carbon olefins from oxygen-containing compound, the selectivity of low-carbon olefins in the product gas obtained ranges from 93 wt % to 96 wt %.

(5) In the method of the present application, the higher the apparent linear velocity of gas in the reaction zone of the fluidized bed reactor, the higher methanol flux can be obtained such that the methanol processing capacity per unit volume of the corresponding device can be increased and the weight hourly space velocity of methanol can reach a range from 5 $h^{-1}$ to 20 $^{-1}$. The spent catalyst zone is used to extract heat to reduce the temperature of the spent catalyst, and deliver low-temperature spent catalyst to the reaction zone so as to increase the bed density in the reaction zone and control the bed temperature in the reaction zone. When the apparent linear velocity of gas ranges from 0.5 m/s to 7.0 m/s, the corresponding bed density ranges from 500 $kg/m^3$ to 100 $kg/m^3$.

(6) The fluidized bed reactor of the present application adopts a structure in which the first gas-solid separation device is directly connected to the delivery pipe, thereby realizing the rapid separation of the gas including low-carbon olefins and the spent catalyst in the stream B, and avoiding the further reaction of low-carbon olefins under the action of the spent catalyst to generate hydrocarbon by product with larger molecular weight.

Figure 1:
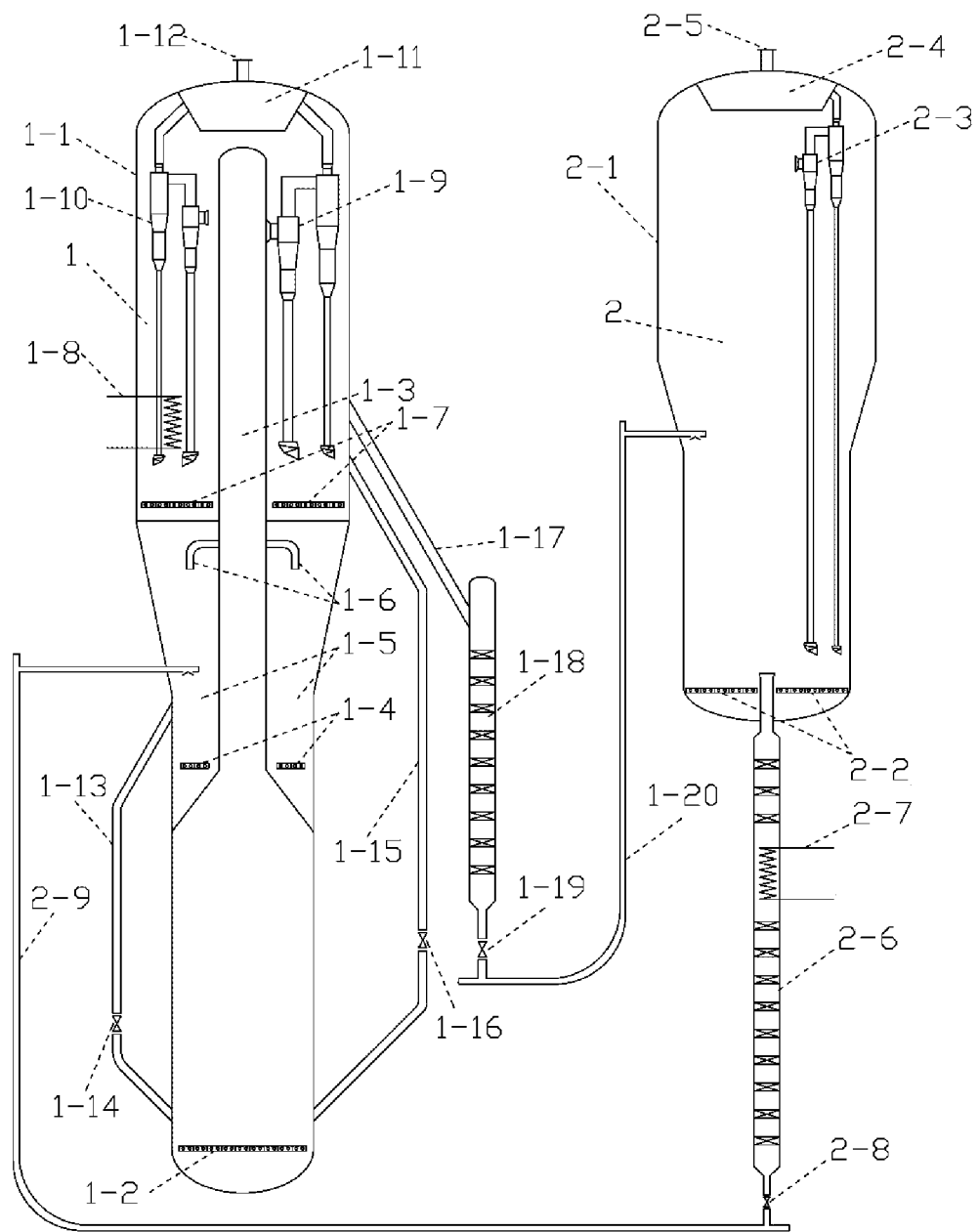
FIG. 1 is a schematic diagram of an oxygen-containing compound to light olefin (DMTO) device according to an embodiment of the present application.
Figure 2:
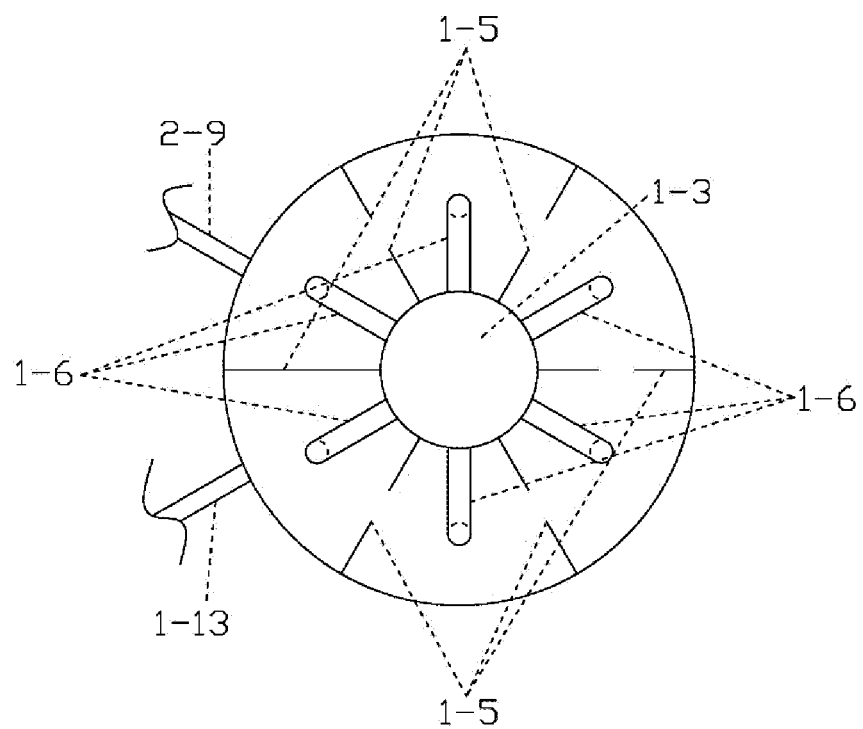
FIG. 2 is a schematic cross-sectional view of a coke control zone of a fluidized bed reactor according to an embodiment of the present application.

The reference signs in FIG. 1 and FIG. 2 are explained as follows:

1 fluidized bed reactor; 1-1 reactor shell; 1-2 reaction zone distributor; 1-3 delivery pipe; 1-4 coke control zone distributor; 1-5 baffle; 1-6 coke control zone gas delivery pipe; 1-7 spent catalyst zone distributor;
1-8 fluidized bed reactor heat extractor; 1-9 first gas-solid separation device; 1-10 second gas-solid separation device; 1-11 gas collection chamber; 1-12 product gas delivery pipe; 1-13 coke controlled catalyst delivery pipe; 1-14 coke controlled catalyst slide valve; 1-15 spent catalyst circulation pipe; 1-16 spent catalyst circulation slide valve; 1-17 spent catalyst inclination pipe; 1-18 first stripper; 1-19 spent catalyst slide valve; 1-20 spent catalyst delivery pipe; 2 fluidized bed regenerator; 2-1 regenerator shell; 2-2 regenerator distributor; 2-3 regenerator gas-solid separation device; 2-4 regenerator gas collection chamber;
2-5 flue gas delivery pipe; 2-6 second stripper; 2-7 regenerator heat extractor; 2-8 regenerated catalyst slide valve; 2-9 regenerated catalyst delivery pipe.

DETAILED DESCRIPTION OF THE EMBODIMENTS

The present application will be described in detail below with reference to the examples, but the present application is not limited to these examples.

Unless otherwise specified, the raw materials and catalyst in the examples of the present application are all commercially available.

The SAPO molecular sieve used in the examples of the present application is available from Zhongke Catalysis (Dalian) Co., Ltd.

In order to improve the catalysis performance of the DMTO catalyst, the present application provides a method for modifying the DMTO catalyst online through the coke control reaction, which includes following steps:

(1) feeding the catalyst to the coke control zone;
(2) feeding the coke control raw material(s) to the coke control zone;
(3) subjecting the coke control material(s) to contact with the catalyst to react in the coke control zone such that the coke control material(s) is coked on the catalyst, wherein the coked catalyst is called the coke controlled catalyst, and the coke content in the coke controlled catalyst ranges from 4 wt % to 9 wt %, the coke species include polymethylbenzene and polymethylnaphthalene, the total weight of which in the total coke weight is ≥70 wt %, and the weight of the coke species with molecular weight of >184 in the total coke weight is ≤25 wt %; and
(4) feeding the coke controlled catalyst to the reaction zone.

Said catalyst is a DMTO catalyst with a coke content ≤3 wt %, and the active component of the DMTO catalyst is SAPO molecular sieve.

The reaction temperature of the coke control reaction ranges from 300° C. to 700° C.

The present application also provides a method for preparing low-carbon olefins by oxygen-containing compounds which includes the method for modifying of the DMTO catalyst on-line through the coke control reaction, and the device used therefor. The device includes a fluidized bed reactor 1 and a fluidized bed regenerator 2.

A device for producing low-carbon olefins from oxygen-containing compound includes a fluidized bed reactor 1 which is divided from bottom to top into a reaction zone, a coke control zone, a spent catalyst zone and a gas-solid separation zone. The fluidized bed reactor 1 includes a reactor shell 1-1, a reaction zone distributor 1-2, a delivery pipe 1-3, a coke control zone distributor 1-4, a baffle 1-5, a coke control zone gas delivery pipe 1-6, a spent catalyst zone distributor 1-7, a fluidized bed reactor heat extractor 1-8, a first gas-solid separation device 1-9, a second gas-solid separation device 1-10, a gas collection chamber 1-11, a product gas delivery pipe 1-12, a coke controlled catalyst delivery pipe 1-13, a coke controlled catalyst slide valve 1-14, a spent catalyst circulation pipe 1-15, a spent catalyst circulation slide valve 1-16, a spent catalyst inclination pipe 1-17, a first stripper 1-18, a spent catalyst slide valve 1-19 and a spent catalyst delivery pipe 1-20;

the reaction zone distributor 1-2 is located at the bottom of the reaction zone of the fluidized bed reactor 1, and the delivery pipe 1-3 is located at the central part of the fluidized bed reactor 1 and the bottom of the delivery pipe is connected to the top of the reaction zone;

the coke control zone is located above the reaction zone and is provided with n baffles 1-5 therein which divides the coke control zone into n sub-coke control zones, n is an integer and 2≤n≤10; the bottom of each sub-coke control zone is independently provided with a coke control zone distributor 1-4; the cross section of the coke control zone is annular in shape, and the cross section of the sub-coke control zone is fan in shape; the first to n sub-coke control zones are concentrically arranged in sequence; the baffles 1-5 can be provided with catalyst circulation hole (s), but the baffles 1-5 between the first sub-coke control zone and the nth sub-coke control zone are not provided with catalyst circulation hole (s); the outlet of the regenerated catalyst delivery pipe 2-9 is connected to the first sub-coke control zone in the fluidized bed reactor 1, and the inlet of the coke controlled catalyst delivery pipe 1-13 is connected to the nth coke control zone; the coke controlled catalyst delivery pipe 1-13 is provided with a coke controlled catalyst slide valve 1-14, and the outlet of the coke controlled catalyst delivery pipe 1-13 is connected to the lower part of the reaction zone, the upper part of the sub-coke control zone is provided with the coke control zone gas delivery pipe 1-6, and the outlet of the coke control zone gas delivery pipe 1-6 is located at the upper part of the sub-coke control zone, and the outlet of the gas delivery pipe 1-6 in the coke control zone is connected to the delivery pipe 1-3;

the spent catalyst zone distributor 1-7 is located at the bottom of the spent catalyst zone, and the fluidized bed reactor heat extractor 1-8 is located at the spent catalyst zone;

the first gas-solid separation device 1-9, the second gas-solid separation device 1-10, and the gas collection chamber 1-11 are located in the gas-solid separation zone of the fluidized bed reactor 1; the inlet of first gas-solid separation device 1-9 is connected to the upper part of the delivery pipe 1-3, the gas outlet of the first gas-solid separation device 1-9 is connected to the gas collection chamber 1-11, and the catalyst outlet of the first gas-solid separation device 1-9 is located in the spent catalyst zone; the inlet of the second gas-solid separation device 1-10 is located in the gas-solid separation zone of the fluidized bed reactor 1, and the gas outlet of the second gas-solid separation device 1-10 is connected to the gas collection chamber 1-11, the catalyst outlet of the second gas-solid separation device 1-10 is located in the spent catalyst zone; the product gas delivery pipe 1-12 is connected to the top of the gas collection chamber 1-11;

the inlet of the spent catalyst circulation pipe 1-15 is connected to the spent catalyst zone, the outlet of the spent catalyst circulation pipe 1-15 is connected to the bottom of the reaction zone, and the spent catalyst circulation pipe 1-15 is provided with a spent catalyst circulation slide valve 1-16;

the inlet of the spent catalyst inclination pipe 1-17 is connected to the spent catalyst zone, the outlet of the spent catalyst inclination pipe 1-17 is connected to the upper part of the first stripper 1-18, and the first stripper 1-18 is placed outside the reactor shell 1-1; an inlet of the spent catalyst slide valve 1-19 is connected to the bottom of the first stripper 1-18 via a pipe, and the outlet of the spent catalyst slide valve 1-19 is connected to an inlet of the spent catalyst delivery pipe 1-20 via a pipe; an outlet of the spent catalyst delivery pipe 1-20 is connected to the middle part of the fluidized bed regenerator 2.

In a preferred embodiment, the first gas-solid separation device 1-9 adopts one or more groups of gas-solid cyclones, and each group of gas-solid cyclones includes one first-stage gas-solid cyclone and one second-stage gas-solid cyclone.

In a preferred embodiment, the second gas-solid separation device 1-10 adopts one or more groups of gas-solid cyclones, and each group of gas-solid cyclones includes one first-stage gas-solid cyclone and one second-stage gas-solid cyclone.

In a preferred embodiment, the second gas-solid separation device 1-10 is a section of pipeline, the inlet of which is located in the gas-solid separation zone, and the outlet of which is connected to the gas collection chamber 1-11.

A device for producing low-carbon olefins from oxygen-containing compound including a fluidized bed regenerator 2 which includes the followings: a regenerator shell 2-1, a regenerator distributor 2-2, a regenerator gas-solid separation device 2-3, a regenerator gas collection chamber 2-4, a flue gas delivery pipe 2-5, a second stripper 2-6, a regenerator heat extractor 2-7, a regenerated catalyst slide valve 2-8 and a regenerated catalyst delivery pipe 2-9;

the regenerator distributor 2-2 is located at the bottom of the fluidized bed regenerator 2, the regenerator gas-solid separation device 2-3 is located at the upper part of the fluidized bed regenerator 2, and the inlet of the regenerator gas-solid separation device 2-3 is located at the upper part of the fluidized bed regenerator 2, the gas outlet of the regenerator gas-solid separation device 2-3 is connected to the regenerator gas collection chamber 2-4, and the regenerated catalyst outlet of the regenerator gas-solid separation device 2-3 is located at the lower part of the fluidized bed regenerator 2, the regenerator gas collection chamber 2-4 is located at the top of the fluidized bed regenerator 2, and the flue gas delivery pipe 2-5 is connected to the top of the regenerator gas collection chamber 2-4; and the second stripper 2-6 is located outside the regenerator shell 2-1, and the inlet pipe of the second stripper 2-6 penetrates the regenerator shell 2-1 and opens above the regenerator distributor 2-2, the regenerator heat extractor 2-7 is located in the second stripper 2-6, the inlet of the regenerated catalyst slide valve 2-8 is connected to the bottom of the second stripper 2-6 via a pipe, and the outlet of regenerated catalyst slide valve 2-8 is connected to the inlet of the regenerated catalyst delivery pipe 2-9 via a pipe, and the outlet of the regenerated catalyst delivery pipe 2-9 is connected to the first sub-coke control zone in the fluidized bed reactor 1.

In a preferred embodiment, the regenerator gas-solid separation device 2-3 adopts one or more groups of gas-solid cyclones, and each group of gas-solid cyclones includes one first-stage gas-solid cyclone and one second-stage gas-solid cyclone.

According to another aspect of the present application, there is also provided a method for producing low-carbon olefins from oxygen-containing compound, which is performed by using at least one of the above-mentioned devices, the method including following steps:

(1) feeding the coke control material into the coke control zone of the fluidized bed reactor 1 from the coke control zone distributor 1-4, and feeding the catalyst from the regenerated catalyst delivery pipe 2-9 into the coke control zone of the fluidized bed reactor 1, subjecting the coke control raw material to contact with the catalyst to perform chemical reaction in the coke control zone to generate the coke controlled catalyst and the coke control product gas; feeding the coke controlled catalyst sequentially into the first to nth sub-coke control zone via the catalyst circulation holes on the baffles 1-5, and then into the reaction zone of the fluidized bed reactor 1 via the coke controlled catalyst delivery pipe 1-13 and the coke controlled catalyst slide valve 1-14, feeding the coke control product gas into the delivery pipe 1-3 via the coke control zone gas delivery pipe 1-6; feeding the raw material including oxygen-containing compound into the reaction zone of the fluidized bed reactor 1 from the reaction zone distributor 1-2 to contact with the coke controlled catalyst to generate the stream A containing low-carbon olefins and the spent catalyst, mixing the stream A and the coke control product gas in the delivery pipe 1-3 to form the stream B which enters the first gas-solid separation device 1-9 via the delivery pipe 1-3 and is divided into the gas phase stream C and the solid phase stream D after the gas-solid separation, wherein the gas phase stream C is gas containing low-carbon olefins and the solid phase stream D is the spent catalyst, feeding the gas phase stream C into the gas collection chamber 1-11, and the solid phase stream D into the spent catalyst zone, feeding a fluidizing gas for the spent catalyst zone into the spent catalyst zone from the spent catalyst zone distributor 1-7 to contact with the spent catalyst such that the fluidizing gas for the spent catalyst zone and the spent catalyst carried by such gas form a stream E, feeding stream E into the second gas-solid separation device 1-10 and dividing the stream E into the gas-phase stream F and the solid-phase stream G after gas-solid separation, wherein the gas phase stream F is the fluidizing gas for the spent catalyst zone, and the solid phase stream G is the spent catalyst, feeding the gas phase stream F into the gas collection chamber 1-11, feeding the solid phase stream G into the spent catalyst zone, mixing the gas phase stream C and the gas phase stream F in the gas collection chamber 1-11 to form the product gas, feeding the product gas into the section downstream via the product gas delivery pipe 1-12; returning one part of the spent catalyst to the bottom of the reaction zone of the fluidized bed reactor 1 via the spent catalyst circulation pipe 1-15 and the spent catalyst circulation slide valve 1-16, feeding the other part of the spent catalyst into the first stripper 1-18 via the spent catalyst inclination pipe 1-17, and after the stripping, feeding the spent catalyst into the middle part of the fluidized bed regenerator 2 via the spent catalyst slide valve 1-19 and the spent catalyst delivery pipe 1-20;

(2) feeding the regeneration gas into the bottom of the fluidized bed regenerator 2 from the regenerator distributor 2-2, subjecting the regeneration gas to contact with the spent catalyst to perform a chemical reaction in the fluidized bed regenerator 2, wherein a part of the coke in the spent catalyst is burned and eliminated to generate a stream H containing flue gas and the regenerated catalyst, feeding the stream H into the regenerator gas-solid separation device 2-3, and dividing the steam H into flue gas and regenerated catalyst after gas-solid separation, feeding the flue gas into the regenerator gas collection chamber 2-4, and then into the flue gas treatment system downstream via the flue gas delivery pipe 2-5, returning the regenerated catalyst to the bottom of the fluidized bed regenerator 2, and then into the second stripper 2-6, and after stripping and heat extraction, into the coke control zone of the fluidized bed reactor 1 via regenerated catalyst slide valve 2-8 and regenerated catalyst delivery pipe 2-9.

In a preferred embodiment, the coke control raw materials consists of: 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water.

In a preferred embodiment, the oxygen-containing compound in the method is methanol, dimethyl ether or a mixture of methanol and dimethyl ether.

In a preferred embodiment, the fluidizing gas for the spent agent zone in the method is nitrogen, water vapor or a mixture of nitrogen and water vapor.

In a preferred embodiment, the regeneration gas in the method consists of 0 wt % to 100 wt % of air, 0 wt % to 50 wt % of oxygen, 0 wt % to 50 wt % of nitrogen, and 0 wt % to 50 wt % of water vapor.

In a preferred embodiment, the active component of the catalyst is SAPO molecular sieve.

In a preferred embodiment, the coke content in the regenerated catalyst is ≤3 wt %.

In a preferred embodiment, the coke content in the coke controlled catalyst ranges from 4 wt % to 9 wt %, the quartile deviation of the coke content distribution in the coke controlled catalyst is less than 1 wt %, and the coke species include polymethylbenzene and polymethylnaphthalene, the total weight of which in the total coke weight is >70 wt %, and the weight of the coke species with molecular weight of >184 in the total coke weight is ≤25 wt %.

In a preferred embodiment, the coke content in the spent catalyst ranges from 9 wt % to 13 wt %; more preferably, the coke content in the spent catalyst is ranges from 10 wt % to 12 wt %.

In a preferred embodiment, the process operating conditions in the coke control zone of the fluidized bed reactor 1 are as follows: the apparent linear velocity of gas ranges from 0.1 m/s to 0.5 m/s, the reaction temperature ranges from 300° C. to 700° C., the reaction pressure ranges from 100 kPa to 500 kPa, and the bed density ranges from 400 kg/m$^3$ to 800 kg/m$^3$.

In a preferred embodiment, the process operating conditions in the reaction zone of the fluidized bed reactor 1 are as follows: the apparent linear velocity of gas ranges from 0.5 m/s to 7.0 m/s, the reaction temperature ranges from 350° C. to 550° C., the reaction pressure ranges from 100 kPa to 500 kPa, and the bed density ranges from 100 kg/m$^3$ to 500 kg/m$^3$.

In a preferred embodiment, the process operating conditions in the spent catalyst zone of the fluidized bed reactor 1 are as follows: the apparent linear velocity of gas ranges from 0.1 m/s to 1.0 m/s, the reaction temperature ranges from 350° C. to 550° C., the reaction pressure ranges from 100 kPa to 500 kPa, and the bed density ranges from 200 kg/m$^3$ to 800 kg/m$^3$.

In a preferred embodiment, the process operating conditions in the fluidized bed regenerator 2 are as follows: the apparent linear velocity of gas ranges from 0.5 m/s to 2.0 m/s, the regeneration temperature ranges from 600° C. to 750° C., the regeneration pressure ranges from 100 kPa to 500 kPa, and the bed density ranges from 150 kg/m³ to 700 kg/m³.

In the method of the present application, the product gas consist of from 38 wt % to 58 wt % ethylene, 35 wt % to 57 wt % propylene, ≤4 wt % $C_4$-$C_6$ hydrocarbons and ≤4 wt % other components, wherein the other components are methane, ethane, propane, hydrogen, CO and $CO_2$ and so on, and the total selectivity of ethylene and propylene in the product gas ranges from 93 wt % to 96 wt %.

For the calculation of the unit consumption of production in the present application, the weight of dimethyl ether in the oxygen-containing compound is equivalently converted to the weight of methanol based on the weight of element C, and the unit of the unit consumption of production is ton of methanol/ton of low-carbon olefins.

In the method in the present application, the unit consumption of production ranges from 2.50 to 2.58 tons of methanol/ton of low-carbon olefins.

In order to better describe the present application and facilitate the understanding of the technical solutions in the present application, typical but non-limiting examples in the present application are as follows.

EXAMPLE 1

This example adopts the device shown in FIG. 1 and FIG. 2. The coke control zone in the fluidized bed reactor includes two baffles, that is, n=2. The coke control zone includes two sub-coke control zones, and the second gas-solid separation device adopts a plurality of groups of gas-solid cyclones, each group of gas-solid cyclones includes one first stage gas-solid cyclone and one second stage gas-solid cyclone.

In this example, the coke control raw material is a mixture of 6 wt % butane, 81 wt % butene, 2 wt % methanol and 11 wt % water; the oxygen-containing compound is methanol; the fluidizing gas for the spent catalyst zone is nitrogen; the regeneration gas is air; the active component in the catalyst is SAPO-34 molecular sieve; the coke content in the catalyst is about 1 wt %; the coke content in the coke controlled catalyst is about 4 wt %, wherein the weight content of polymethylbenzene and polymethylnaphthalene in the total coke weight is about 83 wt % and the weight content of coke species with molecular weight >184 in the total coke weight is about 9 wt %; the quartile deviation of the coke content distribution in the coke controlled catalyst is about 0.9 wt %; the coke content in the spent catalyst is about 9 wt %; the process operating conditions in the coke control zone of the fluidized bed reactor are as follows: the apparent linear velocity of gas is about 0.3 m/s, the reaction temperature is about 500° C., the reaction pressure is about 100 kPa, and the bed density is about 600 kg/m³; the process operating conditions in the reaction zone of the fluidized bed reactor are as follows: the apparent linear velocity of gas is about 7.0 m/s, the reaction temperature is about 550° C., the reaction pressure is about 100 kPa, and the bed density is about 100 kg/m³; the process operating conditions in the spent catalyst zone of the fluidized bed reactor are as follows: the apparent linear velocity of gas is about 1.0 m/s, the reaction temperature is about 550° C., the reaction pressure is about 100 kPa, and the bed density is about 200 kg/m³; the process operating conditions in the fluidized bed regenerator are as follows: the apparent linear velocity of gas is about 0.5 m/s, the regeneration temperature is about 700° C., the regeneration pressure is about 100 kPa, and the bed density is about 700 kg/m³.

In this example, the weight hourly space velocity of oxygen-containing compound in the fluidized bed reactor is about 20 and the product gas consists of 58 wt % ethylene, 35 wt % propylene, 3 wt % $C_4$-$C_6$ hydrocarbons and 4 wt % other components, wherein other components are methane, ethane, propane, hydrogen, CO and $CO_2$ and so on. The unit consumption of production is 2.58 tons of methanol/ton of low-carbon olefins.

EXAMPLE 2

This example adopts the device shown in FIG. 1 and FIG. 2. The coke control zone in the fluidized bed reactor includes 10 baffles, that is, n=10. The coke control zone includes 10 sub-coke control zones, and the second gas-solid separation device adopts a plurality of groups of gas-solid cyclones, each group of gas-solid cyclones includes one first stage gas-solid cyclone and one second stage gas-solid cyclone.

In this example, the coke control raw material is a mixture of 22 wt % methane, 24 wt % ethane, 3 wt % ethylene, 28 wt % propane, 4 wt % propylene, 7 wt % hydrogen and 12 wt % water; the oxygen-containing compound is a mixture of 82 wt % methanol and 18 wt % dimethyl ether; the fluidizing gas for the spent catalyst zone is water vapor; the regeneration gas is a mixture of 50 wt % air and 50 wt % water vapor; the active component in the catalyst is SAPO-34 molecular sieve; the coke content in the catalyst is about 3 wt %; the coke content in the coke controlled catalyst is about 9 wt %, wherein the weight content of polymethylbenzene and polymethylnaphthalene in the total coke weight is about 71 wt % and the weight content of coke species with molecular weight >184 in the total coke weight is about 23 wt %; the quartile deviation of the coke content distribution in the coke controlled catalyst is about 0.2 wt %; the coke content in the spent catalyst is about 13 wt %; the process operating conditions in the coke control zone of the fluidized bed reactor are as follows: the apparent linear velocity of gas is about 0.1 m/s, the reaction temperature is about 300° C., the reaction pressure is about 500 kPa, and the bed density is about 800 kg/m³; the process operating conditions in the reaction zone of the fluidized bed reactor are as follows: the apparent linear velocity of gas is about 0.5 m/s, the reaction temperature is about 350° C., the reaction pressure is about 500 kPa, and the bed density is about 500 kg/m³; the process operating conditions in the spent catalyst zone of the fluidized bed reactor are as follows: the apparent linear velocity of gas is about 0.1 m/s, the reaction temperature is about 350° C., the reaction pressure is about 500 kPa, and the bed density is about 800 kg/m³; the process operating conditions in the fluidized bed regenerator are: the apparent linear velocity of gas is about 2.0 m/s, the regeneration temperature is about 600° C., the regeneration pressure is about 500 kPa, and the bed density is about 150 kg/m³.

In this example, the weight hourly space velocity of oxygen-containing compound in the fluidized bed reactor is about 5 and the product gas consists of 38 wt % ethylene, 57 wt % propylene, 4 wt % $C_4$-$C_6$ hydrocarbons and 1 wt % other components, wherein other components are methane, ethane, propane, hydrogen, CO, and $CO_2$ and so on. The unit consumption of production is 2.53 tons of methanol/ton of low-carbon olefins.

EXAMPLE 3

This example adopts the device shown in FIG. 1 and FIG. 2. The coke control zone in the fluidized bed reactor includes 4 baffles, that is, n=4. The coke control zone includes 4 sub-coke control zones. The second gas-solid separation device is a section of pipeline, the inlet of which is located in the gas-solid separation zone, and the outlet of which is connected to the gas collection chamber of the fluidized bed reactor.

In this example, the coke control raw material is a mixture of 1 wt % propane, 1 wt % propylene, 3 wt % butane, 51 wt % butene, 3 wt % pentane, 22 wt % pentene, 1 wt % hexane, 7 wt % hexene, 2 wt % methanol and 9 wt % water; the oxygen-containing compound is dimethyl ether; the fluidizing gas for the spent catalyst zone consists of 5 wt % nitrogen and 95 wt % water vapor; the regeneration gas consists of 50 wt % air and 50 wt % oxygen; the active component in the catalyst is SAPO-34 molecular sieve; the coke content in the catalyst is about 2 wt %; the coke content in the coke controlled catalyst is about 6 wt %, wherein the weight content of polymethylbenzene and polymethylnaphthalene in the total coke weight is about 80 wt % and the weight content of coke species with molecular weight >184 in the total coke weight is about 11 wt %; the quartile deviation of the coke content distribution in the coke controlled catalyst is about 0.6 wt %; the coke content in the spent catalyst is about 11 wt %; the process operating conditions in the coke control zone of the fluidized bed reactor are as follows: the apparent linear velocity of gas is about 0.4 m/s, the reaction temperature is about 700° C., the reaction pressure is about 300 kPa, and the bed density is about 500 kg/m$^3$; the process operating conditions in the reaction zone of the fluidized bed reactor are as follows: the apparent linear velocity of gas is about 3.0 m/s, the reaction temperature is about 450° C., the reaction pressure is about 300 kPa, and the bed density is about 230 kg/m$^3$; the process operating conditions in the spent catalyst zone of the fluidized bed reactor are as follows: the apparent linear velocity of gas is about 0.2 m/s, the reaction temperature is about 450° C., the reaction pressure is about 300 kPa, and the bed density is about 600 kg/m$^3$; the process operating conditions in the fluidized bed regenerator are as follows: the apparent linear velocity of gas is about 1.0 m/s, the regeneration temperature is about 750° C., the regeneration pressure is about 300 kPa, and the bed density is about 360 kg/m$^3$.

In this example, the weight hourly space velocity of oxygen-containing compounds in the fluidized bed reactor is about 9 h$^{-1}$; and the product gas consists of 48 wt % ethylene, 48 wt % propylene, 2 wt % $C_4$-$C_6$ hydrocarbons and 2 wt % other components, wherein other components are methane, ethane, propane, hydrogen, CO and $CO_2$ and so on. The unit consumption of production is 2.50 tons of methanol/ton of low-carbon olefins.

EXAMPLE 4

This example adopts the device shown in FIG. 1 and FIG. 2. The coke control zone in the fluidized bed reactor includes 6 baffles, that is, n=6. The coke control zone includes 6 sub-coke control zones, and the second gas-solid separation device adopts a plurality of groups of gas-solid cyclones, each group of gas-solid cyclones includes one first stage gas-solid cyclone and one second stage gas-solid cyclone.

In this example, the coke control raw material is a mixture of 5 wt % butane, 72 wt % butene, 8 wt % methanol and 15 wt % water; the oxygen-containing compound is methanol; the fluidizing gas for the spent catalyst zone consists of 73 wt % nitrogen and 27 wt % water vapor; the regeneration gas is a mixture of 50 wt % air and 50 wt % nitrogen; the active component in the catalyst is SAPO-34 molecular sieve; the coke content in the catalyst is about 2 wt %; the coke content in the coke controlled catalyst is about 6 wt %, wherein the weight content of polymethylbenzene and polymethylnaphthalene in the total coke weight is about 77 wt % and the weight content of coke species with molecular weight >184 in the total coke weight is about 16 wt %; the quartile deviation of the coke content distribution in the coke controlled catalyst is about 0.3 wt %; the coke content in the spent catalyst is about 12 wt %; the process operating conditions in the coke control zone of the fluidized bed reactor are as follows: the apparent linear velocity of gas is about 0.5 m/s, the reaction temperature is about 600° C., the reaction pressure is about 200 kPa, and the bed density is about 400 kg/m$^3$; the process operating conditions of the reaction zone of the fluidized bed reactor are as follows: the apparent linear velocity of gas is about 4.0 m/s, and the reaction temperature is about 500° C., the reaction pressure is about 200 kPa, and the bed density is about 160 kg/m$^3$; the process operating conditions in the spent catalyst zone of the fluidized bed reactor: the apparent linear velocity of gas is about 0.5 m/s, the reaction temperature is about 500° C., the reaction pressure is about 200 kPa, and the bed density is about 300 kg/m$^3$; the process operating conditions in the fluidized bed regenerator are as follows: the apparent linear velocity of gas is about 1.5 m/s, and the regeneration temperature is about 680° C., the regeneration pressure is about 200 kPa, and the bed density is about 280 kg/m$^3$.

In this example, the weight hourly space velocity of oxygen-containing compounds in the fluidized bed reactor is about 13 h$^{-1}$; and the product gas consists of 53 wt % ethylene, 42 wt % propylene, 4 wt % $C_4$-$C_6$ hydrocarbons and 1 wt % other components, wherein other components are methane, ethane, propane, hydrogen, CO and $CO_2$ and so on. The unit consumption of production is 2.52 tons of methanol/ton of low-carbon olefins.

Comparative Example

The difference between this comparative example and Example 4 is that: this comparative example does not employ the coke control reaction to modify the DMTO catalyst online, and the coke control raw material is nitrogen which is an inert gas and will not change the properties of the regenerated catalyst in the coke control zone. In other words, the catalyst fed into the reaction zone is a regenerated catalyst.

In this example, the product gas consists of 44 wt % ethylene, 38 wt % propylene, 10 wt % $C_4$-$C_6$ hydrocarbons and 8 wt % other components, wherein the other components are methane, ethane, propane, hydrogen, CO and $CO_2$ and so on. The unit consumption of production is 2.92 tons of methanol/ton of low-carbon olefins.

This comparative example shows that the online modification of DMTO catalyst by coke control reaction can greatly improve the performance of the catalyst and reduce the unit consumption of production.

The above examples are only illustrative, and do not limit the present application in any form. Any change or modification, made by the skilled in the art based on the technical content disclosed above, without departing from the spirit of the present application, is equivalent example and falls within the scope of the present application.

What is claimed is:

1. A fluidized bed reactor, comprising a reactor shell, a reaction zone, a coke control zone, and a delivery pipe;
   wherein the reactor shell comprises a lower shell and an upper shell, the lower shell encloses the reaction zone, the delivery pipe is disposed above the reaction zone and the delivery pipe is in communication with the reaction zone, an outer periphery of the delivery pipe is provided with the upper shell, the upper shell and the delivery pipe enclose to form a cavity comprising the coke control zone;

an upper part of the delivery pipe is provided with a gas outlet;

the reaction zone comprises a reaction raw material inlet and a coke controlled catalyst inlet;

the coke control zone comprises a catalyst inlet, a coke controlled catalyst outlet, a coke control gas outlet, and a coke control raw material inlet;

the coke control zone is an annular cavity;

n baffles are arranged in the coke control zone, and the n baffles divide the coke control zone into n sub-coke control zones, the n sub-coke control zones comprise a first sub-coke control zone, a second sub-coke control zone, and an nth sub-coke control zone;

at least one catalyst circulation hole is provided on each of n-1 of the n baffles so that a catalyst flows in an annular shape in the coke control zone, wherein n is an integer; and the catalyst inlet is arranged in the first sub-coke control zone, the coke controlled catalyst outlet is arranged in the nth sub-coke control zone, and the coke control gas outlet is arranged between two adjacent baffles of the n baffles.

2. The fluidized bed reactor according to claim 1, wherein 2≤n≤10;

a cross section of the coke control zone is annular in shape, and a cross section of the sub-coke control zone is fan in shape;

the coke control gas outlet is connected to the delivery pipe by a coke control zone gas delivery pipe;

a coke control zone distributor is provided at a bottom of each of the n sub-coke control zones; the coke control raw material inlet is in communication with the coke control zone distributor, or the coke control raw material inlet is located below the coke control zone distributor;

a reaction zone distributor is arranged at the reaction raw material inlet, and the reaction zone distributor is arranged at a bottom of the reaction zone.

3. The fluidized bed reactor according to claim 1, further comprising a spent catalyst zone, wherein the spent catalyst zone is arranged above the coke control zone and sleeved on the outer periphery of the delivery pipe, wherein a partition plate is provided between the spent catalyst zone and the coke control zone; and a spent catalyst zone distributor is arranged at a bottom of the spent catalyst zone;

the spent catalyst zone comprises a heat extractor for the fluidized bed reactor;

the fluidized bed reactor further comprises a gas-solid separation zone, the gas-solid separation zone is arranged above the spent catalyst zone and the gas-solid separation zone is sleeved on the outer periphery of the delivery pipe; the gas-solid separation zone is provided with a gas-solid separation device; and the spent catalyst zone is in communication with the gas-solid separation zone;

the gas-solid separation device comprises a first gas-solid separation device and a second gas-solid separation device; an inlet of the first gas-solid separation device is in communication with the delivery pipe, and a catalyst outlet of the first gas-solid separation device is located in the spent catalyst zone; and a catalyst outlet of the second gas-solid separation device is provided in the spent catalyst zone;

the fluidized bed reactor further comprises a product gas delivery pipe and a gas collection chamber, the product gas delivery pipe and the gas collection chamber are arranged on an upper part of the reactor shell, wherein the product gas delivery pipe is arranged at a top of the reactor shell, and the product gas delivery pipe is connected to a top of the gas collection chamber; and a gas outlet of the second gas-solid separation device is connected to the gas collection chamber, and a gas outlet of the first gas-solid separation device is connected to the gas collection chamber;

the fluidized bed reactor further comprises a spent catalyst circulation pipe, the spent catalyst circulation pipe is arranged outside the reactor shell; wherein an inlet of the spent catalyst circulation pipe is connected to the spent catalyst zone, and an outlet of the spent catalyst circulation pipe is connected to a bottom of the reaction zone.

4. A method for producing low-carbon olefins from an oxygen-containing compound using the fluidized bed reactor according to claim 1.

5. The method according to claim 4, comprising the following steps:

feeding a coke control raw material and the catalyst from a regenerator into the coke control zone to react to generate a coke controlled catalyst and a coke control product gas;

wherein the catalyst forms an annular flow through the at least one catalyst circulation hole on each of n−1 of the n baffles;

the method comprises the following steps:

(1) feeding the coke control raw material from a coke control zone distributor into the coke control zone, and feeding the catalyst from the catalyst inlet to the coke control zone, wherein the coke control raw material and the catalyst contact to react in the coke control zone to generate the coke controlled catalyst and the coke control product gas; wherein the coke controlled catalyst enters the reaction zone via the coke controlled catalyst outlet, and the coke control product gas enters the delivery pipe via the coke control gas outlet; and (2) feeding a raw material containing the oxygen-containing compound into the reaction zone via the reaction raw material inlet, to contact with the coke controlled catalyst, to obtain a first stream comprising the low-carbon olefins.

6. The method according to claim 5, wherein, the coke control raw material comprises a $C_1$-$C_6$ hydrocarbon compound;

the $C_1$-$C_6$ hydrocarbon compound is at least one of $C_1$-$C_6$ alkanes and $C_1$-$C_6$ olefins.

7. The method according to claim 6, wherein the coke control raw material further comprises at least one of hydrogen, an alcohol compound, and water; and a total content of the alcohol compound and the water in the coke control raw material is greater than or equal to 10 wt % and less than or equal to 50 wt %;

the alcohol compound is at least one of methanol and ethanol.

8. The method according to claim 7, wherein, the coke control raw material comprises: 0 wt % to 20 wt % of the hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of the methanol, 0 wt % to 50 wt % of the ethanol, and 0 wt % to 50 wt % of the water; and a weight content of the $C_1$-$C_6$ hydrocarbon compound is not zero.

9. The method according to claim 5, wherein the oxygen-containing compound is at least one of methanol and dimethyl ether;

the catalyst comprises an SAPO molecular sieve; a coke content in the coke controlled catalyst ranges from 4 wt % to 9 wt %; and a quartile deviation of a coke content distribution in the coke controlled catalyst is less than 1 wt %.

10. The method according to claim 9, wherein coke species in the coke controlled catalyst comprise polymethylbenzene and polymethylnaphthalene;

a total weight content of the polymethylbenzene and the polymethylnaphthalene in a total coke weight is ≥70 wt %;

a weight content of coke species with a molecular weight greater than 184 in the total coke weight is ≤25 wt %;

wherein the total coke weight refers to a total weight of the coke species.

11. The method according to claim 5, wherein process operating conditions in the coke control zone are as follows: an apparent linear velocity of gas ranges from 0.1 m/s to 0.5 m/s, a reaction temperature ranges from 300° C. to 700° C., a reaction pressure ranges from 100 kPa to 500 kPa, and a bed density ranges from 400 kg/m³ to 800 kg/m³;

process operating conditions in the reaction zone are as follows: an apparent linear velocity of gas ranges from 0.5 m/s to 7.0 m/s, a reaction temperature ranges from 350° C. to 550° C., a reaction pressure ranges from 100 kPa to 500 kPa, and a bed density ranges from 100 kg/m³ to 500 kg/m³.

12. The method according to claim 5, further comprising the following step after step (2):

(3) mixing the first stream comprising the low-carbon olefins and the coke control product gas flowing out of the coke control gas outlet to form a mixed stream in the delivery pipe, the mixed stream enters a first gas-solid separation device by the delivery pipe, and is then divided into a first gas phase stream and a first solid phase stream after a gas-solid separation, wherein the first gas phase stream is a gas comprising the low-carbon olefins, and the first solid phase stream is a spent catalyst;

the method further comprises the following step after step (3): (4) feeding the first gas phase stream into a gas collection chamber, and the first solid phase stream into a spent catalyst zone, feeding a fluidizing gas for the spent catalyst zone into the spent catalyst zone from a fluidizing gas inlet for the spent catalyst zone to contact with the spent catalyst such that the fluidizing gas for the spent catalyst zone and the spent catalyst carried by the fluidizing gas form a secnod stream;

the method further comprises the following step after step (4): (5) feeding the second stream into a second gas-solid separation device to divide the second stream into a second gas phase stream and a second solid phase stream after the gas-solid separation, wherein the second gas phase stream is the fluidizing gas for the spent catalyst zone, and the second solid phase stream is the spent catalyst; feeding the second gas phase stream into the gas collection chamber, and the second solid phase stream into the spent catalyst zone, and mixing the first gas phase stream and the second gas phase stream in the gas collection chamber to form the coke control product gas, the coke control product gas then enters a section downstream via a product gas delivery pipe;

the method further comprises following step after step (5):

(6) returning a first part of the spent catalyst in the spent catalyst zone to a bottom of the reaction zone of the fluidized bed reactor through a spent catalyst circulation pipe.

13. The method according to claim 9, wherein a coke content in a spent catalyst ranges from 9 wt % to 13 wt %.

14. The method according to claim 12, wherein the fluidizing gas for the spent catalyst zone comprises at least one of nitrogen and water vapor.

15. The method according to claim 12, wherein process operating conditions in the spent catalyst zone are as follows: an apparent linear velocity of gas ranges from 0.1 m/s to 1.0 m/s, a reaction temperature ranges from 350° C. to 550° C., a reaction pressure ranges from 100 kPa to 500 kPa, and a bed density ranges from 200 kg/m³ to 800 kg/m³.

16. A device, comprising the fluidized bed reactor according to claim 1 and a fluidized bed regenerator, wherein the fluidized bed reactor is in communication with the fluidized bed regenerator.

17. The device according to claim 16, wherein the fluidized bed regenerator comprises a regenerator shell;

the regenerator shell is provided with a spent catalyst inlet;

the spent catalyst inlet is in communication with a spent catalyst zone of the fluidized bed reactor;

the spent catalyst inlet is in communication with the spent catalyst zone of the fluidized bed reactor through a first stripper;

a bottom of the regenerator shell is in communication with the coke control zone;

the bottom of the regenerator shell is in communication with the coke control zone through a second stripper.

18. The device according to claim 17, wherein a regenerator heat extractor is provided in the second stripper;

a regenerator distributor is provided in the regenerator shell; and one end of the second stripper extends into the regenerator shell;

the fluidized bed regenerator further comprises a regenerator gas-solid separation device, a regenerator gas collection chamber, and a flue gas delivery pipe; the regenerator gas-solid separation device is provided in the regenerator shell, the regenerator gas collection chamber and the flue gas delivery pipe are provided on an upper part of the regenerator shell, the flue gas delivery pipe is provided on a top of the regenerator shell, and the flue gas delivery pipe is connected to a top of the regenerator gas collection chamber; and a gas outlet of the regenerator gas-solid separation device is connected to the regenerator gas collection chamber, and a regenerated catalyst outlet of the regenerator gas-solid separation device is provided at a lower part of the regenerator shell.

19. The method according to claim 12, further comprising feeding a second part of the spent catalyst in the spent catalyst zone into a fluidized bed regenerator, and then feeding the catalyst regenerated in the fluidized bed regenerator into the coke control zone;

the method comprises the following steps:

(a) passing the second part of the spent catalyst through a first stripper, and then feeding the the second part of the spent catalyst into a middle of the fluidized bed regenerator after a stripping;

(b) feeding a regeneration gas from a regeneration gas inlet into a bottom of the fluidized bed regenerator to contact with the second part of the spent catalyst to perform a chemical reaction to generate a third stream comprising a flue gas and the catalyst regenerated, the third stream enters a regenerator gas-solid separation device and the third stream is divided into the flue gas and the catalyst regenerated after the gas-solid separation, feeding the flue gas into a regenerator gas collection chamber and then into a flue gas treatment system downstream through a flue gas delivery pipe, returning the catalyst regenerated to the bottom of the fluidized bed regenerator, then into a second stripper, and into the coke control zone of the fluidized bed reactor after the stripping and a heat extraction;

the regeneration gas is at least one of oxygen, nitrogen, water vapor and air;

the regeneration gas comprises 0 wt % to 100 wt % of the air, 0 wt % to 50 wt % of the oxygen, 0 wt % to 50 wt % of the nitrogen, and 0 wt % to 50 wt % of the water vapor.

20. The method according to claim 19, wherein process operating conditions in the fluidized bed regenerator are as follows: an apparent linear velocity of gas ranges from 0.5 m/s to 2.0 m/s, a regeneration temperature ranges from 600° C. to 750° C., a regeneration pressure ranges from 100 kPa to 500 kPa, and a bed density ranges from 150 kg/m$^3$ to 700 kg/m$^3$;

a coke content in the catalyst regenerated is ≤3 wt %.

* * * * *